United States Patent [19]

Davis

[11] Patent Number: 4,947,845

[45] Date of Patent: * Aug. 14, 1990

[54] METHOD OF MAXIMIZING CATHETER LONGEVITY IN AN IMPLANTABLE MEDICATION INFUSION SYSTEM

[75] Inventor: Mark W. Davis, Newbury Park, Calif.

[73] Assignee: Pacesetter Infusion, Ltd., Sylmar, Calif.

[*] Notice: The portion of the term of this patent subsequent to Mar. 27, 2007 has been disclaimed.

[21] Appl. No.: 297,506

[22] Filed: Jan. 13, 1989

[51] Int. Cl.$^5$ .................................................. A61B 5/00
[52] U.S. Cl. ..................................... 128/637; 128/630; 604/50
[58] Field of Search ............... 128/630, 632, 637, 668, 128/897-898, DIG. 22; 604/49-50, 52, 266; 424/9

[56] References Cited

U.S. PATENT DOCUMENTS

| | | | |
|---|---|---|---|
| 3,550,581 | 12/1970 | Boyle | 128/637 |
| 4,008,717 | 2/1977 | Kowarski | 128/632 |
| 4,266,021 | 5/1981 | Nylen | 128/632 X |
| 4,731,726 | 5/1988 | Allen | 128/630 X |
| 4,830,013 | 5/1989 | Maxwell | 128/637 |

FOREIGN PATENT DOCUMENTS 1110444  8/1984  U.S.S.R. .............................. 128/630

Primary Examiner—Angela D. Sykes
Attorney, Agent, or Firm—Leslie S. Miller

[57] ABSTRACT

A method of significantly enhancing the period of time that an implanted intraperitoneal catheter used for the delivery of therapeutic medication will operate without encountering significant blockage by fibrotic tissue is disclosed. By monitoring and maintaining certain physical parameters in patients having an implantable catheter below desirable levels for the parameters, catheter survival in the patients is maximized. The four parameters used are blood triglyceride level, blood cholesterol level, the level of insulin dosage per day, and mean blood glucose (MBG) level, with the first two being the more accurate parameters.

21 Claims, 1 Drawing Sheet

METHOD OF MAXIMIZING CATHETER LONGEVITY IN AN IMPLANTABLE MEDICATION INFUSION SYSTEM

IDENTIFICATION OF RELATED PATENT APPLICATIONS

This application is related to concurrently filed copending patent application U.S. Ser. No. 297505, entitled "A Method of Screening and Selecting Intraperitoneal Medication Infusion Pump Candidates," which application is hereby incorporated herein by reference.

BACKGROUND OF THE INVENTION

1. Field of the Invention

The present invention relates generally to the field of implantable medication infusion systems, and more particularly to a method of significantly enhancing the period of time that an implanted intraperitoneal catheter used for the delivery of therapeutic medication will operate without encountering significant blockage probably due to fibrotic tissue.

Metabolism of glucose in the body is a particularly important chemical reaction which allows the utilization of the energy contained in food. The physiological system of the body has a sophisticated regulatory system which, when operating properly, maintains the level of blood glucose at an optimum level, thereby assuring the availability of adequate amounts of glucose when needed by the body.

This glucose regulatory system utilizes insulin to regulate blood glucose in two ways. First, the rate of glucose transport through the cell membrane of many body cell types is increased by insulin. In the absence of insulin, the rate of glucose transport through such cells is dramatically reduced to less than one-fourth the normal rate of glucose transport. However, excessively high insulin levels can greatly increase the rate of glucose transport to five times the normal rate. It is thereby apparent that insulin level has at least the capacity to adjust the rate of glucose absorption in the body by a factor of twenty.

Secondly, insulin acts as a regulatory hormone which is supplied to the liver. The secretion of insulin by the pancreas is stimulated by digestion and the accompanying higher glucose levels in the body, resulting in an increase in the amount of insulin secreted into the portal vein. While approximately half of the insulin secreted into the portal vein is distributed throughout the body by the cardiovascular system, the rest of the insulin is immediately absorbed by the liver. In response to the surge of insulin, the liver produces large quantities of glucokinase, an enzyme enabling conversion of glucose into glycogen, which may be stored by the body. Much of the excess glucose entering the cardiovascular system as a result of digestion is thereby quickly removed to maintain relatively normal levels of glucose concentration in the blood.

When the level of glucose concentration in the blood later begins to drop below normal, the level of insulin secretion by the pancreas is reduced, and production of the hormone glucagon is begun. Glucagon enables the conversion of glycogen in the liver back into glucose by activating liver phosphorylase, an enzyme, and the result is the release of glucose into the cardiovascular system for distribution throughout the body. Once again, the body acts to maintain the concentration of glucose in the blood at a normal level.

The system which maintains a normal level of blood glucose is finely balanced, and the relationship between the pancreas and the liver can be easily upset. The most common problem is the situation when the pancreas no longer secretes adequate levels of insulin, a condition known as "diabetes mellitus." In some instances, the pancreas may completely cease the production of insulin.

In any event, the diminution or reduction in insulin production results in a rise in the concentration of glucose in the blood, which causes the osmotic pressure in extracellular fluids to rise above normal pressure The result of this increase in osmotic pressure is typically significant cellular dehydration. The increase in the blood glucose concentration also affects the kidneys, thereby causing them to act to remove excess glucose from the blood, in which process fluids are further removed from the body.

The diminution of insulin production is also accompanied by a substantial reduction in the transportation of glucose into most tissues of the body. In addition, an insulin shortage also prevents glucose from being stored in the liver as glycogen, thereby resulting in a lack of available glucose in the times of glucose need. In conditions in which there is an absence of sufficient levels of glucose, body cell metabolism becomes fat based instead of carbohydrate based. Heavy dependence on fat metabolism due to insufficient blood glucose concentration results in a substantial rise in the concentration of acetoacetic acid and other keto acids to as much as thirty times normal levels, thereby causing a significant reduction in the pH of blood below its normal pH level of 7.4.

When the kidneys attempt to alleviate the concentration of the various keto acids in the blood, substantial amounts of sodium are also removed, thereby further lowering the blood pH. Should the blood pH fall below 7.0, a coma state will typically be experienced, with the results frequently being fatal.

Diabetic treatment has centered on restoring proper carbohydrate metabolism by the administration of insulin. For years insulin has been administered by multiple daily injections into the peripheral circulation, either by intramuscular or subcutaneous injection, or shot, using a syringe and needle to delivers the insulin dosage to the patient at intervals up to four times a day.

As an alternative to periodic injections, the relatively recent addition of small, portable insulin infusion pumps has come as a welcome improvement. Insulin infusion pumps are utilized to administer insulin to a subcutaneous injection location in a patient in small, metered doses in an essentially continuous manner. Infusion pump therapy may be electronically controlled to deliver precise, metered doses at exactly determined intervals, thereby providing a beneficial gradual infusion of medication to the patient. In this manner, the insulin infusion pump is able to mimic the natural process by delivering both a basal rate of insulin delivery and boluses of insulin whereby overall delivery of insulin is maintained more precisely.

However, peripheral insulin administration to a subcutaneous location results in only about ten percent of the insulin administered reaching the liver, as compared to the fifty percent or so in normal individuals. Therefore, rather than hepatic glucose production being lowered first, blood glucose level is reduced due to the presence of higher than normal levels of insulin in the peripheral circulation by an increased utilization of glucose by body tissues. It is more difficult to maintain a normal level of blood glucose by using insulin injection or subcutaneous insulin infusion, since, unlike the natural feedback system of the body, hepatic glucose production is not substantially decreased by insulin which is injected or infused peripherally.

It is therefore apparent that it is desirable to administer insulin to a patient in a manner whereby a greater percentage of the insulin reaches the liver than in peripheral administration of insulin. An implantable infusion pump connected to a catheter which would deliver insulin internally rather than peripherally may be used to accomplish this objective, but since the pump and catheter are internally implanted, they have to be capable of continuing to function effectively over an extended period of time.

Such an implantable insulin pump is disclosed in U.S. Pat. No. 4,373,527, to Fischell, in U.S. Pat. No. 4,573,994, to Fischell et al., in U.S. Pat. No. 4,525,165 to Fischell, and in U.S. Pat. No. 4,731,051, to Fischell.

The problem with implantable catheters is that they rapidly tend to become overgrown with fibrotic tissue which will close off the catheter in short order. This is particularly true in those cases where only a small flow of medication is being delivered through the catheter. Several types of catheters have been used, with the most common being a simple tube having an aperture therethrough. At the end of the tube, the aperture allows medication to exit the tube and enter the body. It will be appreciated that such an arrangement is susceptible to being covered with fibrotic tissue relatively rapidly, since the fibrotic tissue will grow around the end of the tube.

Variations include the addition of a disk which is mounted at the end of the catheter with the tube leading orthogonally to the disk with medication exiting the aperture of the tube at the center of the disk. While this design is somewhat less susceptible to clogging by the rapid growth of fibrotic tissue, in time the entire disk will be covered and the opening will be closed by parietal or fibrotic tissue. The other approach that has been used is to make the opening of a small diameter to cause the fluid to exit the catheter with a relatively high velocity.

Another approach to an implantable catheter is illustrated in U.S. Pat. Application Ser. No. 043,796, filed on Apr. 29, 1987, to Diaz et al. This application is assigned to the assignee of the present application, and is hereby incorporated herein by reference. With the catheter of the Diaz et al. invention, an implantable catheter having a novel catheter terminator configuration having a recessed area which inhibits the ability of fibrotic tissue to choke off fluid delivered through the catheter is implanted in the tissue of the omentum. The distal or delivery end is placed into a fold in the omentum tissue, which is then sutured around the delivery end of the catheter.

Placement of the Diaz et al. catheter causes the insulin to be absorbed effectively in a manner mimicking to the greatest extent possible the body's utilization of insulin. The terminator of the catheter is held in a secure location, with predictable absorption of the insulin. In addition, fibrotic tissue growth may happen at a somewhat reduced pace from other locations in the body, and occlusion of the aperture is prevented by the fact that the recessed area is spaced away from the place where fibrotic tissue will grow.

It will be appreciated that the placement and the configuration of even the Diaz et al. implantable catheter leaves something to be desired. Since the implantation of a catheter generally involves major surgery, it is desirable that an implantable catheter be capable of operating over an extended period of time without requiring repair or replacement. It seems that the obstruction of any catheter design will occur over a period of time in the body due to the body's natural defense mechanism.

Accordingly, it is the primary objective of the present invention to maximize catheter longevity in a patient having an implanted pump and catheter. As such, it is an objective to delineate criteria which will optimize, to the extent possible, the period of time that an implantable catheter will continue to function effectively to deliver insulin or other therapeutic medication. The criteria will accordingly reduce the likelihood of subsequent surgery to repair or replace an obstructed catheter, and as such represent substantial advantage in the selection of appropriate patients to whom the benefits of implantation far outweigh the possible risks. The criteria must also present no adverse effects or incur any substantial relative disadvantage in their implementation. It may therefore be perceived that the advantages of the method comprising the present invention will result in extending to the maximum degree possible the operating life of an implantable catheter, making the method of the present invention a highly desirable enhancement to implantable medication infusion system therapy.

SUMMARY OF THE INVENTION

The disadvantages and limitations of the background art discussed above are overcome by the present invention. With this invention, a method is taught which will enable patients who have received an implanted catheter to maximize the likelihood that the catheter will not become obstructed. According to the method of the present invention, one or more measured parameters are used to determine the probability that the catheter will become obstructed.

It has been discovered in clinical research performed on patients having an implanted pump and catheter that by maintaining these parameters at or below certain defined levels, the likelihood of encountering an obstructed catheter is substantially diminished. In fact, the probability of encountering an obstructed catheter may be reduced by as much as over 90 percent by maintaining one or more of the monitored parameters at or below certain defined levels. This represents an astonishing potential reduction in what has been to date the most serious complication in the implantation of an implantable insulin pump and catheter.

It has been determined that four parameters which may be monitored and varied by personal conduct at or below certain levels are indicative of the likelihood of an obstructed catheter. High levels in two of these parameters, blood triglyceride level and blood cholesterol level, are highly indicative of the likelihood of catheter blockage. High levels in the other two parameters, the amount of insulin dosage per day and mean blood glucose (MBG) level are also quite indicative of the likelihood of catheter blockage.

Accordingly, by monitoring one or more of these parameters and by altering conduct to maintain the levels of these parameters below certain levels the likelihood of a blocked catheter may be substantially reduced. It has been recognized that diet is particularly important with respect to all four of the parameters. In addition, exercise can be utilized to reduce insulin dosage required, and to a lesser extent, the level of mean blood glucose.

By establishing highly accurate criteria for promoting the longevity of an implanted catheter, the chance that the catheter will be obstructed is minimized. Accordingly, it will be realized at once that by so doing, the requirement of replacement surgery is also minimized, and that patient discomfort due to surgery is alleviated. There are also other health benefits inherent in maintaining the parameter levels required by the present invention. The benefits of the present invention with respect to monitoring and maintaining triglyceride level, cholesterol level, and mean blood glucose are also applicable to all patients having an implanted catheter, not just insulin pump patients.

It may therefore be seen that the present invention maximizes catheter longevity in a patient having an implanted catheter. The criteria delineated to maximize catheter longevity optimize, to the greatest extent possible, the period of time that an implantable catheter will continue to function effectively to deliver insulin or other therapeutic medication. The criteria also present no adverse effects, and do not incur any substantial relative disadvantage in their implementation. It will therefore be perceived that the advantages of the method comprising the present invention result in extending to the maximum degree possible the operating life of an implantable catheter, making the method of the present invention a highly desirable enhancement to implantable medication infusion system therapy.

DESCRIPTION OF THE DRAWINGS

These and other advantages of the present invention are best understood with reference to the drawings, in which.

DETAILED DESCRIPTION OF THE PREFERRED EMBODIMENT

The preferred embodiment of the present invention utilizes a method which will enable patients who have received an implanted catheter to maximize the likelihood that the catheter will not become obstructed. According to this method, one or more measured parameters are used to determine the probability that the catheter will become obstructed. By modifying personal habits such as diet and the level of exercise engaged in, all of these measured parameters may be controlled to a degree, thereby modifying the parameters in the desired manner to greatly reduce the possibility of catheter blockage.

As mentioned above, it has been discovered in clinical research performed on patients having an implanted pump and catheter that when the levels of one or more of the parameters are above certain predefined levels, the risk of catheter blockage is substantially increased. By establishing a program to establish and/or maintain these parameters at or below the predefined levels in all patients having an implanted catheter, the likelihood of encountering an obstructed catheter is substantially diminished. It has been established in clinical studies that the probability of encountering an obstructed catheter may be reduced by as much as over 90 percent by maintaining one or more of the monitored parameters at or below reduction in what has been to date by far the most serious complication in the implantable pump therapy.

In the clinical studies, it has been determined that there are at least four parameters which may be monitored to provide an indication of the likelihood of continued catheter implantation without blockage. All four of these parameters may be controlled, at least to a degree, by varying personal conduct. In many cases, all four of the parameters may be controlled to ensure that they remain at or below certain levels which indicative a substantially decreased likelihood of encountering an obstructed catheter. The four parameters are blood triglyceride level, blood cholesterol level, the level of insulin dosage per day, and mean blood glucose (MBG) level.

High levels in two of these parameters, blood triglyceride level and blood cholesterol level, have been found to be highly indicative of a substantially increased likelihood of catheter blockage. High levels in the other two parameters, the level of insulin dosage per day and mean blood glucose (MBG) level, have also been found to be quite indicative of an increased likelihood of catheter blockage. The level of insulin dosage per day is the easiest of the parameters to monitor The other three parameters, blood triglyceride level, blood cholesterol level, and mean blood glucose (MBG) level may be monitored by periodically taking blood samples and performing an analysis on the samples.

Figure 1A:
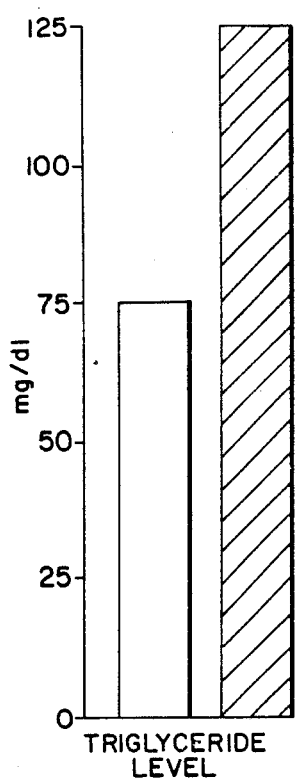
FIG. 1A is a graph comparing clinically measured triglyceride levels between a first population who after implantation of a pump and catheter have not experienced a clogged or obstructed catheter and a second population who after implantation of a pump and catheter have experienced a clogged or obstructed catheter.

First, with regard to blood triglyceride level, the clinically measured levels of triglyceride are shown in FIG. 1A. The bar on the left side of FIG. 1A represents the triglyceride levels of a first population who have not experienced a clogged or obstructed catheter. The average triglyceride level of this first population is 75.41 mg/dl.

The cross-hatched bar on the right side of FIG. 1A represents the triglyceride levels of a second population who at some point have experienced or will experience a clogged or obstructed catheter. The average triglyceride level of this second population is 125.75 mg/dl. Thus, the levels of triglyceride in the second population who at some point have experienced or will experience a clogged or obstructed catheter are substantially higher than the levels of triglyceride in the first population who have not experienced a clogged or obstructed catheter.

Figure 1B:
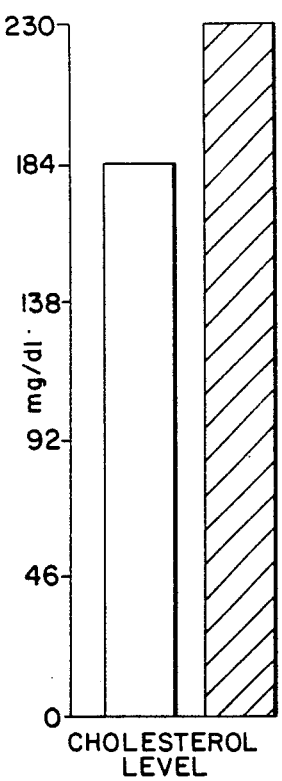
FIG. 1B is a graph comparing clinically measured cholesterol levels between a first population who after implantation of a pump and catheter have not experienced a clogged or obstructed catheter and a second population who after implantation of a pump and catheter have experienced a clogged or obstructed catheter.

Secondly, with regard to cholesterol level, the clinically measured levels of cholesterol are shown in FIG. 1B. The bar on the left side of FIG. 1B represents the cholesterol levels of the first population who have not experienced a clogged or obstructed catheter. The average cholesterol level of the first population is 184.71 mg/dl.

The cross-hatched bar on the right side of FIG. 1B represents the cholesterol levels of the second population who at some point have experienced or will experience a clogged or obstructed catheter. The average cholesterol level of the second population is 229.75 mg/dl. Thus, the levels of cholesterol in the second population who at some point have experienced or will experience a clogged or obstructed catheter are substantially higher than the levels of cholesterol in the first population who have not experienced a clogged or obstructed catheter.

Figure 1C:
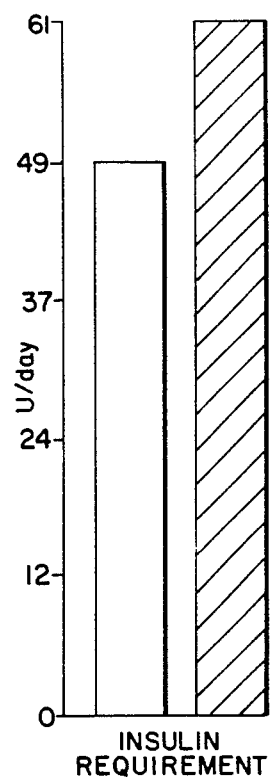
FIG. 1C is a graph comparing clinically monitored insulin requirements between a first population who after implantation of a pump and catheter have not experienced a clogged or obstructed catheter and a second population who after implantation of a pump and catheter have experienced a clogged or obstructed catheter.

Next, with regard to the level of insulin dosage per day, the clinically measured levels of insulin dosage per day are shown in FIG. 1C. The bar on the left side of FIG. 1C represents the levels of insulin dosage per day of the first population who have not experienced a clogged or obstructed catheter. The average level of insulin dosage per day of the first population is 49.07 Units per day.

The cross-hatched bar on the right side of FIG. 1C represents the levels of insulin dosage per day of the second population who at some point have experienced or will experience a clogged or obstructed catheter. The average level of insulin dosage per day of the second population is 61.2 Units per day. Thus, the levels of insulin dosage per day in the second population who at some point have experienced or will experience a clogged or obstructed catheter are higher than the levels of insulin dosage per day in the first population who have not experienced a clogged or obstructed catheter.

Figure 1D:
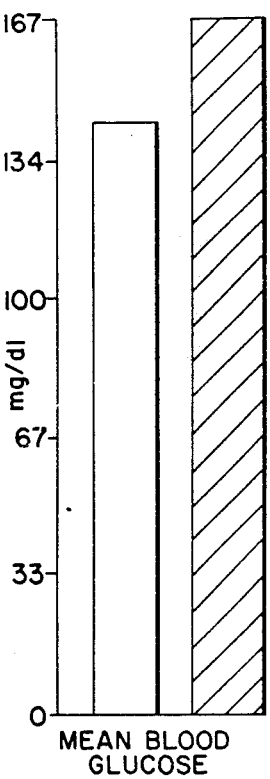
FIG. 1D is a graph comparing clinically measured mean blood glucose levels between a first population who after implantation of a pump and catheter have not experienced a clogged or obstructed catheter and a second population who after implantation of a pump and catheter have experienced a clogged or obstructed catheter.

Finally, with regard to the level of mean blood glucose, the clinically measured levels of mean blood glucose are shown in FIG. 1D. The bar on the left side of FIG. 1D represents the levels of mean blood glucose of the first population who have not experienced a clogged or obstructed catheter. The average level of mean blood glucose of the first population is 142.2 mg/dl.

The cross-hatched bar on the right side of FIG. 1D represents the levels of mean blood glucose of the second population who at some point have experienced or will experience a clogged or obstructed catheter. The average level of mean blood glucose of the second population is 167 mg/dl. Thus, the levels of mean blood glucose in the second population who at some point have experienced or will experience a clogged or obstructed catheter are higher than the levels of mean blood glucose in the first population who have not experienced a clogged or obstructed catheter.

Based on the clinical testing, it is possible to establish levels for the four parameters above which there is an indication of a substantial risk of catheter blockage. For triglyceride level, this level is between 110 and 125 mg/dl, with 120 mg/dl being the level of the preferred embodiment. For cholesterol level, the indicator level is between 180 and 235 mg/dl, with 200 to 215 mg/dl representing the preferred level.

For the level of insulin dosage per day, this level is between 55 and 85 Units per day, with 60 Units per day being the level of the preferred embodiment of the present invention. Finally, the level of mean blood glucose is between 145 mg/dl and 175 mg/dl, with 150 mg/dl being the preferred level. The reductions of risk achieved by maintaining the four parameters within the levels suggested above may be discussed with reference to FIGS. 2A, 2B, 2C, and 2D.

Figure 2A:
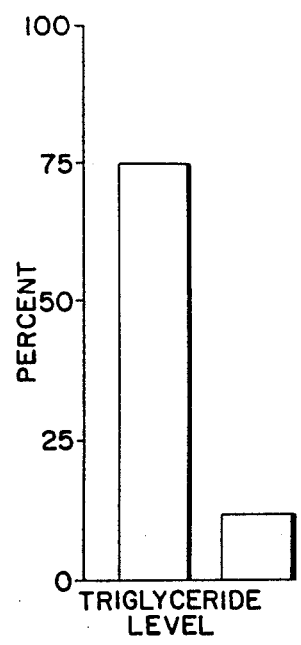
FIG. 2A is a graph demonstrating the effectiveness of the method of the present invention in maintaining a patient on an implanted pump and catheter without clogging or obstruction of the catheter by maintaining triglyceride levels below 120 mg/dl (milligrams per deciliter)

Referring first to FIG. 2A, the bar demonstrates the effectiveness of the method of the present invention in using measured triglyceride level as criteria for preventing patients who have an implanted pump and catheter from experiencing clogging or obstruction of the catheter. It may be seen that of the patients who have a triglyceride level of 120 mg/dl or below, over 92 percent will not develop a clogged catheter, as predicted by the use of triglyceride level as a sole criteria.

This 92 percent level is felt to represent an acceptable degree of risk. Patients above the 120 mg/dl level would be strongly encouraged to lower their triglyceride level below 120 mg/dl. This may be accomplished by a change in diet. By lowering their triglyceride level below 120 mg/dl, their risk of encountering an obstructed catheter would drop by over 90 percent. The use of triglyceride as a criteria will produce a false positive less than six percent of the time. The high degree of accuracy in predicting which patients are likely to encounter an obstructed catheter and the low risk of a false positive makes triglyceride level an excellent criteria for the method of the present invention.

Figure 2B:
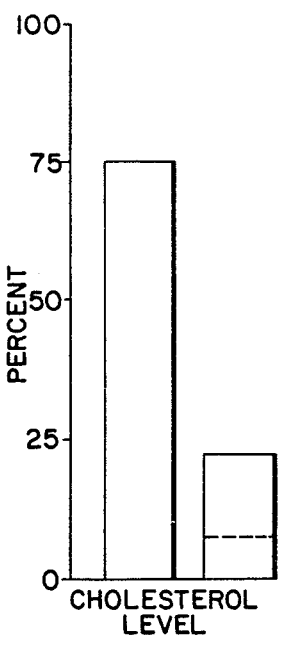
FIG. 2B is a graph demonstrating the effectiveness of the method of the present invention in maintaining a patient on an implanted pump and catheter without clogging or obstruction of the catheter by maintaining cholesterol levels below 215 mg/dl.

Referring next to FIG. 2B, the bar demonstrates the effectiveness of the method of the present invention in using measured cholesterol level as a criteria for preventing patients who have an implanted pump and catheter from experiencing clogging or obstruction of the catheter. It may be seen that of the patients who have a cholesterol level of 215 mg/dl or below, over 92 percent will not develop a clogged catheter, as predicted by the use of cholesterol level as a sole criteria. By using a cholesterol level of 210 mg/dl or below as the criteria, over 90 percent will not develop a clogged catheter, as shown by the dotted line in FIG. 2B.

This 90 to 92 percent level is felt to represent an acceptable degree of risk. Patients above the 200 to 215 mg/dl level would be strongly encouraged to lower their cholesterol level below 200 mg/dl. This may be accomplished by a change in diet. By lowering their cholesterol level below 200 mg/dl, their risk of encountering an obstructed catheter would drop by nearly 80 percent. The use of cholesterol as a criteria will produce a false positive less than six percent of the time at the 215 mg/dl level, and approximately 22 percent of the time at the 200 mg/dl level. The high degree of accuracy in predicting which patients are likely to encounter an obstructed catheter and the low risk of a false positive makes cholesterol level an excellent criteria for the method of the present invention.

Figure 2C:
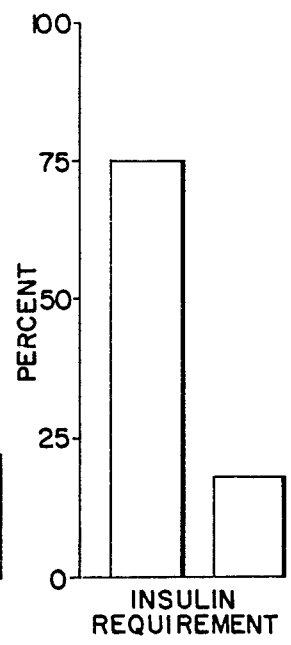
FIG. 2C is a graph demonstrating the effectiveness of the method of the present invention in maintaining a patient on an implanted pump and catheter without clogging or obstruction of the catheter by maintaining insulin requirements below 60 Units per day.

Referring now to FIG. 2C, the bar demonstrates the effectiveness of the method of the present invention in using measured the level of insulin dosage per day as a criteria for preventing patients who have an implanted pump and catheter from experiencing clogging or obstruction of the catheter. It may be seen that of the patients who have a level of insulin dosage per day of 60 Units per day or below, over 91 percent will not develop a clogged catheter, as predicted by the use of the level of insulin dosage per day as a sole criteria.

This 91 percent level is felt to represent an acceptable degree of risk. Patients above the 60 Units per day level would be strongly encouraged to lower their level of insulin dosage per day below 60 Units per day. This may be accomplished primarily by moderate exercise. A person going from a sedentary lifestyle to one of moderate exercise can lower insulin requirements by as much as one-third. A change in diet may also prove helpful, particularly if carbohydrate intake is reduced. By lowering their level of insulin dosage per day below 60 Units per day, their risk of encountering an obstructed catheter could drop by over 80 percent. The use of the level of insulin dosage per day as a criteria will produce a false positive approximately 16 percent of the time. The degree of accuracy in predicting which patients are likely to encounter an obstructed catheter and the degree of error makes level of insulin dosage per day a good criteria for the method of the present invention; however, it would be better in combination with one of the other criteria.

Figure 2D:
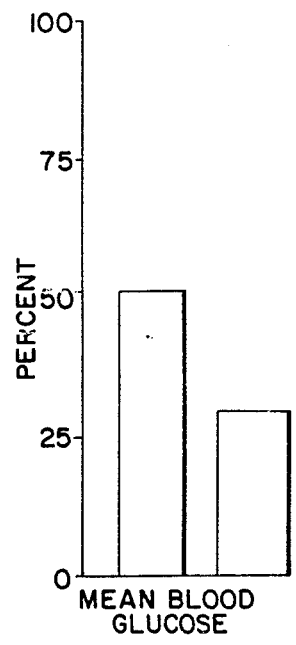
FIG. 2D is a graph demonstrating the effectiveness of the method of the present invention in maintaining a patient on an implanted pump and catheter without clogging or obstruction of the catheter by maintaining mean blood glucose levels below 150 mg/dl.

Referring finally to FIG. 2D, the bar demonstrates the effectiveness of the method of the present invention in using measured mean blood glucose level as a criteria for preventing patients who have an implanted pump and catheter from experiencing clogging or obstruction of the catheter. It may be seen that of the patients who have a mean blood glucose level of 150 mg/dl or below, over 81 percent will not develop a clogged catheter, as predicted by the use of triglyceride level as a sole criteria.

This 81 percent level is felt to represent an acceptable degree of risk. Patients above the 150 mg/dl level would be encouraged to lower their mean blood glucose level below 150 mg/dl. This may be accomplished primarily by a change in diet. By lowering the intake of carbohydrates mean blood glucose can be substantially lowered. Exercise may also have a smaller effect on lowering mean blood glucose. By lowering their mean blood glucose level below 150 mg/dl, their risk of encountering an obstructed catheter would drop by over 35 percent. The use of mean blood glucose as a criteria will produce a false positive less than 28 percent of the time. Of the four parameters, mean blood glucose level is the poorest criteria for the method of the present invention; however, it may be useful in combination with one or more of the other criteria.

Accordingly, by monitoring one or more of these parameters and by altering conduct to maintain the levels of these parameters below certain levels, the likelihood of a blocked catheter may be substantially reduced. It has been recognized that diet is particularly important with respect to all four of the parameters. In addition, exercise can be utilized to reduce insulin dosage required, and to a lesser extent, the level of mean blood glucose. By maintaining all four of the criteria below the indicated levels, it is believed that the longevity of catheter survival in the patient may be maximized.

It may thus be appreciated by those skilled in the art from the above detailed description of the preferred embodiment that by establishing highly accurate criteria which indicate beneficial longevity of an implanted catheter, the chance that the catheter will be obstructed is greatly reduced, by as much as over 90 percent. Accordingly, it will be realized that by so doing, the requirement of replacement surgery is effectively minimized, and that patient discomfort due to surgery is substantially alleviated. There are also other health benefits inherent in maintaining the parameter levels required by the present invention.

The method of the present invention enhances catheter longevity in a patient having an implanted catheter, using the criteria delineated to maximize the period of time that the implantable catheter will continue to function effectively to deliver insulin or other therapeutic medication. The method of the present invention presents no adverse effects, and does not incur any substantial relative disadvantage in its implementation. The benefits of the present invention with respect to monitoring and maintaining triglyceride level, cholesterol level, and mean blood glucose are applicable to all patients having an implanted catheter, not just diabetic insulin pump patients. It will therefore be perceived that the advantages of the method of the present invention make it a highly desirable enhancement to implantable medication infusion system therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, combinations, and alterations should therefore be seen as within the scope of the present invention.

What is claimed is:

1. A method of enhancing the period of time that an implanted intraperitoneal catheter used for the delivery of therapeutic medication will operate in a patient without encountering significant blockage, comprising:
   determining in a patient the level of at least one parameter from the group of parameters consisting of blood triglyceride level, blood cholesterol level, the level of insulin dosage per day, and mean blood glucose (MBG) level;
   comparing the determined level of said at least one parameter with a predetermined maximum value for said at least one parameter to determine whether said at least one parameter is greater than said predetermined maximum value or not; and
   providing an indication of increased risk of catheter blockage if said at least one parameter is greater than said predetermined maximum value.

2. A method as defined in claim 1, wherein said at least one parameter is blood triglyceride level.

3. A method as defined in claim 2, wherein said predetermined maximum value is between approximately 100 mg/dl and 125 mg/dl.

4. A method as defined in claim 3, wherein said predetermined maximum value is approximately 120 mg/dl.

5. A method as defined in claim 1, wherein said at least one parameter is blood cholesterol level.

6. A method as defined in claim 5, wherein said predetermined maximum value is between approximately 180 mg/dl and 235 mg/dl.

7. A method as defined in claim 6, wherein said predetermined maximum value is between approximately 200 mg/dl and 215 mg/dl.

8. A method as defined in claim 7 wherein said predetermined maximum value is approximately 200 mg/dl.

9. A method as defined in claim 1, wherein said at least one parameter is the level of insulin dosage per day.

10. A method as defined in claim 9, wherein said predetermined maximum value is between approximately 55 Units per day and 85 Units per day.

11. A method as defined in claim 10, wherein said predetermined maximum value is approximately 60 Units per day.

12. A method as defined in claim 1, wherein said at least one parameter is mean blood glucose (MBG) level.

13. A method as defined in claim 12, wherein said predetermined maximum value is between approximately 145 mg/dl and 175 mg/dl.

14. A method as defined in claim 13, wherein said predetermined maximum value is approximately 150 mg/dl.

15. A method as defined in claim 1, additionally comprising:
attempting to cause a reduction in said at least one parameter if an indication of increased risk of catheter blockage is provided due to said at least one parameter being greater than said predetermined maximum value.

16. A method of enhancing the period of time that an implanted intraperitoneal catheter used for the delivery of therapeutic medication will operate in a patient without encountering significant blockage, comprising:
determining the level of triglycerides in the blood of a patient;
comparing the determined level of triglycerides with a predetermined maximum value for triglycerides to determine whether the determined level of triglycerides is greater than said predetermined maximum value for triglycerides or not;
providing an indication of increased risk of catheter blockage if the determined level of triglycerides is greater than said predetermined maximum value for triglycerides;
determining the level of cholesterol in the blood of a patient;
comparing the determined level of cholesterol with a predetermined maximum value for cholesterol to determine whether the determined level of cholesterol is greater than said predetermined maximum value for cholesterol or not;
providing an indication of increased risk of catheter blockage if the determined level of cholesterol is greater than said predetermined maximum value for cholesterol;
determining the level of insulin dosage per day of a patient;
comparing the determined level of insulin dosage per day with a predetermined maximum value for insulin dosage per day to determine whether the determined level of insulin dosage per day is greater than said predetermined maximum value for insulin dosage per day or not;
providing an indication of increased risk of catheter blockage if the determined level of insulin dosage per day is greater than said predetermined maximum value for insulin dosage per day;
determining the level of mean blood glucose (MBG) in the blood of a patient;
comparing the determined level of mean blood glucose with a predetermined maximum value for mean blood glucose to determine whether the determined level of mean blood glucose is greater than said predetermined maximum value for mean blood glucose or not; and
providing an indication of increased risk of catheter blockage if the determined level of mean blood glucose is greater than said predetermined maximum value for mean blood glucose.

17. A method of enhancing the period of time that an implanted intraperitoneal catheter used for the delivery of therapeutic medication will operate in a patient without encountering significant blockage, comprising:
determining the level of triglycerides in the blood of a patient;
comparing the determined level of triglycerides with a predetermined maximum value for triglycerides to determine whether the determined level of triglycerides is greater than said predetermined maximum value for triglycerides or not;
providing an indication of increased risk of catheter blockage if the determined level of triglycerides is greater than said predetermined maximum value for triglycerides;
determining the level of cholesterol in the blood of a patient;
comparing the determined level of cholesterol with a predetermined maximum value for cholesterol to determine whether the determined level of cholesterol is greater than said predetermined maximum value for cholesterol or not; and
providing an indication of increased risk of catheter blockage if the determined level of cholesterol is greater than said predetermined maximum value for cholesterol.

18. A method of enhancing the period of time that an implanted intraperitoneal catheter used for the delivery of therapeutic medication will operate in a patient without encountering significant blockage, comprising:
determining the level of triglycerides in the blood of a patient;
comparing the determined level of triglycerides with a predetermined maximum value for triglycerides to determine whether the determined level of triglycerides is greater than said predetermined maximum value for triglycerides or not; and
providing an indication of increased risk of catheter blockage if the determined level of triglycerides is greater than said predetermined maximum value for triglycerides.

19. A method of enhancing the period of time that an implanted intraperitoneal catheter used for the delivery of therapeutic medication will operate in a patient without encountering significant blockage, comprising:

determining the level of cholesterol in the blood of a patient;

comparing the determined level of cholesterol with a predetermined maximum value for cholesterol to determine whether the determined level of cholesterol is greater than said predetermined maximum value for cholesterol or not; and providing an indication of increased risk of catheter blockage if the determined level of cholesterol is greater than said predetermined maximum value for cholesterol.

20. A method of enhancing the period of time that an implanted intraperitoneal catheter used for the delivery of therapeutic medication will operate in a patient without encountering significant blockage, comprising:

determining the level of insulin dosage per day of a patient;

comparing the determined level of insulin dosage per day with a predetermined maximum value for insulin dosage per day to determine whether the determined level of insulin dosage per day is greater than said predetermined maximum value for insulin dosage per day or not; and providing an indication of increased risk of catheter blockage if the determined level of insulin dosage per day is greater than said predetermined maximum value for insulin dosage per day.

21. A method of enhancing the period of time that an implanted intraperitoneal catheter used for the delivery of therapeutic medication will operate in a patient without encountering significant blockage, comprising:

determining the level of mean blood glucose (MBG) in the blood of a patient;

comparing the determined level of mean blood glucose with a predetermined maximum value for mean blood glucose to determine whether the determined level of mean blood glucose is greater than said predetermined maximum value for mean blood glucose or not; and providing an indication of increased risk of catheter blockage if the determined level of mean blood glucose is greater than said predetermined maximum value for mean blood glucose.

* * * * *